United States Patent [19]

Collins

[11] 4,338,842
[45] Jul. 13, 1982

[54] SAMPLER FOR MOLTEN MATERIAL AND ENTRANCE TUBE THEREFOR

[76] Inventor: William J. Collins, 7005 Madison St., Merrillville, Ind. 46410

[21] Appl. No.: 277,264

[22] Filed: Jun. 25, 1981

Related U.S. Application Data

[62] Division of Ser. No. 75,941, Sep. 17, 1979, Pat. No. 4,297,902.

[51] Int. Cl.³ ............................................. G01N 1/20
[52] U.S. Cl. ................................ 73/863.52; 73/864.55
[58] Field of Search ........... 73/863.41, 863.51, 863.52, 73/863.53, 863.54, 863.55, 863.58, 864.53, 864.55, 864.56, 864.57

[56] References Cited

U.S. PATENT DOCUMENTS

| | | | |
|---|---|---|---|
| 1,967,428 | 7/1934 | Quereau | 73/863.61 |
| 3,638,476 | 2/1972 | Paterson | 73/863.51 |
| 3,803,921 | 4/1974 | Dieterich | 73/863.51 |
| 4,002,071 | 1/1977 | Collins | 73/863.51 |

*Primary Examiner*—S. Clement Swisher
*Attorney, Agent, or Firm*—Charles S. Penfold

[57] ABSTRACT

The invention involves providing a device for sampling molten material which, among other things, comprises a pair of mating sections, each of which preferably has a rear recessed enlargement or head and a reduced front semi-cylindrical extension which when assembled provide a chamber and a tubular formation the latter of which is adapted to accommodate a tube which serves to receive such a material for flow into the chamber.

The invention particularly involves providing a tube with a unique form of an entrance.

10 Claims, 5 Drawing Figures

SAMPLER FOR MOLTEN MATERIAL AND ENTRANCE TUBE THEREFOR

This application is a Division of my application Ser. No. 075,941 filed Sept. 17, 1979 which has issued as U.S. Pat. No. 4,297,902 dated Nov. 3, 1981.

SUMMARY OF THE INVENTION

Reference is also hereby made to my copending application Ser. No. 173,486 filed July 30, 1980.

Appreciable development has been conducted by engineers with respect to providing various forms of devices for obtaining samples of molten material and many patents have issued directed to such devices. Quite a number of patents have issued to applicant in this regard and many are directed to devices, comprising, among other things, a pair of mating sections, each having a rear recessed head and a reduced front channel. These sections when assembled provide a chamber and a tubular formation in which a tubular inlet is secured for receiving molten material for flow into the chamber to obtain a sample.

OBJECTIVES

With the foregoing in mind, the primary object of the subject invention is to provide a tube which is adapted for use with such a device as described in the preceding paragraph or a device in which each of the mating sections comprises a head provided with a recess and a tubular formation of the character described in my application Ser. No. 075,941 filed Sept. 17, 1979 and the fore end of the tube is provided with a unique entrance whereby to facilitate entry of such material into the device for obtaining a sample.

More particularly, the object is to provide a tube in which front marginal edges thereof define what may be termed an inclined notch or entrance which serves to enlarge the normal internal cross-dimension or diameter of the tube and thereby promote the inflow of the material when the tube is inserted into a supply of such a material.

Also, an object of the invention is to provide a conventional tube with a detachable fitting or accessory which is provided with an inclined notch in lieu of providing it in the tube.

Other objects reside in providing structure having components which can be manufactured and assembled on a production basis and one which is efficient in obtaining a sample.

Additional objects and advantages of the structure will become apparent after the description hereinafter set forth is considered in conjunction with the drawings annexed hereto.

DRAWINGS

DESCRIPTION

Figure 1:
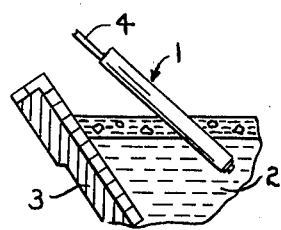
FIG. 1 is a pictorial view showing the use of one form of a sampler device in obtaining a sample of molten material from a vessel containing such a material.

Referring first to FIG. 1 there is shown a sampler structure or device generally designated 1 immersed in a mass of molten material 2 in a vessel 3. A lance 4 is detachably connected to the device for manipulating the latter. The structure or device generally designated 1 is described in my copending application above referred to and although it is employed to obtain a sample in a different way from a supply of molten material or hot liquid the tube at its fore end may be constructed to embody the subject invention.

Figure 2:
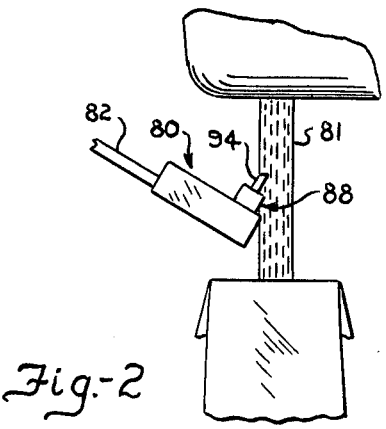
FIG. 2 is a pictorial view showing a modified device being utilized to obtain a sample from a stream of molten material.
Figure 3:
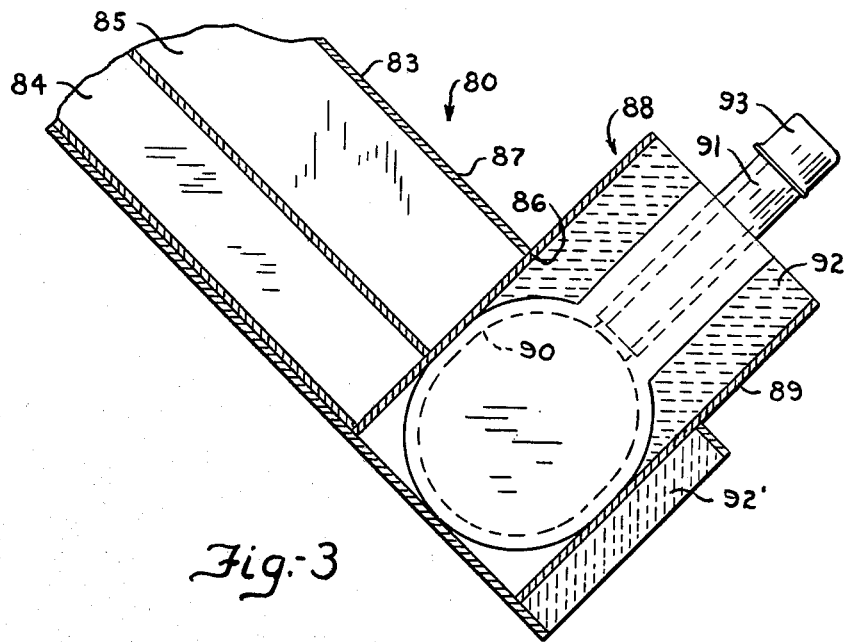
FIG. 3 is an enlarged section of the device shown in FIG. 2.

FIG. 2 depicts a structure or device generally designated 80 for use in obtaining a sample of molten material from a stream 81 thereof, structural details of the device being generally illustrated in FIG. 3. A lance 82 is detachably connectible to the device for manipulating it into and from the stream.

The structure of FIG. 3, preferably comprises an elongated tubular housing 83 provided with internal structure forming a pair of tubular formations 84 and 85 of which 84 is preferably utilized to accommodate the lance 82. A fore extremity of the housing is provided with an opening 86 in a side wall 87 thereof and a subassembly or device generally designated 88 is secured in the opening to locate it substantially transverse to the longitudinal axis of the housing.

The device 88 includes a casing 89 and a pair of mating sections are disposed in this casing and form a chamber 90 for receiving a sample of molten material which is adapted for inflow through a tubular means or tube 91. The sections are preferably held in the casing by a mass of cement or insulating material 92 which substantially surrounds reduced portions of the sections and additional cement 92' fills a void at the fore end of the housing 87 for the purposes of protection and stabilization. The tube 91 extends forwardly of the cement and a cap or closure 93 is preferably attached to the free end of the tube for the purpose of initially preventing the inflow of slag or foreign matter if the device is utilized for obtaining a sample from a mass in a vessel as depicted in FIG. 1 or if used according to FIG. 2 to obtain a sample from the stream 81 a tube such as 94 shown in FIG. 4 is preferably employed.

It is to be understood that the use of all of the structures or devices shown and described above can be utilized to obtain samples of molten material from any supply thereof, whether from a vessel or stream and that they are modifiable because their use depends in some measure on the character and liquidity of the material to be sampled. Otherwise expressed, the devices are designed and constructed for maximum versatility or convertability.

Figure 4:
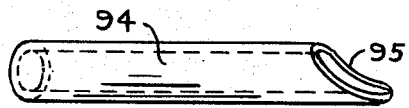
FIG. 4 is a pictorial view of a tube or tubular means which is usable with the device of FIG. 3.

FIG. 4 shows a tubular means or tube 94, preferably constructed of a non-metallic material, such as Pyrex or quartz, for use in different sampling devices, including those described above. More specifically the tube is provided with a curved side notch 95 whereby to facilitate entry of molten material into the tube, as distinguished from a straight bevelled entrance.

Figure 5:
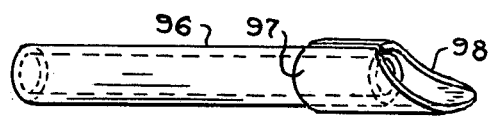
FIG. 5 is a pictorial view of a tube or tubular means provided with a fitting whereby to facilitate entry of molten material into the tubular means.

FIG. 5 shows a tube 96 provided with a sleeve 97 which can be readily slipped onto the fore end of the tube whereby to facilitate entry of material through a curved or scalloped entrance 98. This sleeve is preferably of a split cylindrical character so that it is resiliently flexible for clamping onto the tube. The sleeve also serves to protect the fore end of the tube. It should be noted that the sleeve is preferably located so that the fore end of the tube is positioned a predetermined distance inwardly from the fore end of the sleeve so as to promote the inflow of material into the tube.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. An elongated tube for use as a component of a device for obtaining a sample of molten material, and a split sleeve carried by a fore extremity of said tube and having a curved entrance extending a predetermined distance forwardly of said extremity thereof to facilitate entry of such a material into the tube.

2. An elongated member having a resiliently flexible generally tubular extremity for accommodating a fore end of tubular means of a device for obtaining a sample of molten material and an opposite extremity having an enlarged entrance to facilitate entry of such a material.

3. A device for obtaining a sample of molten material from a supply thereof, said device comprising an elongated outer housing having a front extremity provided with wall structure forming a chamber for receiving such a material, an elongated tube having an inner extremity communicating with said chamber and a concave bevelled side entrance at its outer end for initially receiving such a material for flow into said chamber, and said housing having a rear extremity for attachment to a lance.

4. An elongated tube for use as a component of a device for obtaining a sample of molten material from a supply thereof, and a split sleeve carried by a fore extremity of said tube and having an enlarged entrance extending a predetermined distance forwardly of said extremity whereby to facilitate entry of such a material into the tube.

5. An elongated member having a resiliently flexible generally tubular extremity for accommodating a fore end of a tubular means of a device for obtaining a sample of molten material and an opposite extremity having a curved notched entrance whereby to facilitate entry of such a material into the tubular means.

6. A device for obtaining a sample of molten material from a supply thereof, said device comprising an elongated outer housing having a front extremity provided with wall structure forming a chamber for receiving such a material, an elongated tube having an inner extremity communicating with said chamber and an outer notched concave end entrance for initially receiving such a material for flow into said chamber, and said housing being constructed whereby the device can be manipulated to cause the tube to enter such a supply of material.

7. A device for obtaining a sample of molten material from a supply thereof, said device comprising an elongated outer housing having a front extremity provided with wall structure forming a chamber for receiving such a material, an elongated tube having an inner extremity communicating with said chamber and a fore extremity, a split sleeve carried by said fore extremity and having a curved entrance extending a predetermined distance forwardly of this extremity whereby to facilitate flow of such a material into the chamber via said tube.

8. A manipulatable device for obtaining a sample of molten material from a supply thereof, said device comprising an elongated outer housing having a front extremity provided with wall structure forming a chamber, tubular means having an inner extremity communicating with said chamber and a fore end, an elongated member having a resiliently flexible generally tubular inner extremity mounted on said fore end and a front extremity having an enlarged entrance whereby to facilitate entry of such a material into said tube for flow into said chamber, and said housing having a rear extremity offering connection with a lance.

9. A device for obtaining a sample of molten material from a supply thereof, said device comprising an outer elongated housing having a front extremity provided with wall structure forming a chamber for receiving such a material, an elongated tube having an inner extremity communicating with said chamber and a fore extremity, a split sleeve carried by said fore extremity and having an enlarged front entrance extending a predetermined distance forwardly of this extremity whereby to facilitate entry of such a material into said tube for flow into said chamber.

10. A device for obtaining a sample of molten material from a supply thereof, said device comprising a casing containing wall structure forming a chamber, tubular means having an inner extremity communicating with said chamber and a fore end, an elongated member having a resiliently flexible generally tubular extremity accommodating said fore end and a front extremity having a curved notched entrance whereby to facilitate entry of such a material into said tubular means for flow into said chamber.

* * * * *